(12) United States Patent
Iwatschenko

(10) Patent No.: US 7,506,759 B2
(45) Date of Patent: Mar. 24, 2009

(54) METHOD AND DEVICE FOR WETTING A MEDICAL IMPLANT OR TRANSPLANT

(75) Inventor: Peter Iwatschenko, Neunkirchen (DE)

(73) Assignee: MTF MediTech Franken GmbH, Eckental (DE)

(*) Notice: Subject to any disclaimer, the term of this patent is extended or adjusted under 35 U.S.C. 154(b) by 771 days.

(21) Appl. No.: 10/515,235

(22) PCT Filed: Jun. 4, 2003

(86) PCT No.: PCT/EP03/05878

§ 371 (c)(1),
(2), (4) Date: Nov. 22, 2004

(87) PCT Pub. No.: WO03/101342

PCT Pub. Date: Dec. 11, 2003

(65) Prior Publication Data

US 2005/0167309 A1    Aug. 4, 2005

(30) Foreign Application Priority Data

Jun. 4, 2002  (EP) ................... 02012509

(51) Int. Cl.
*B65D 25/00*   (2006.01)
(52) U.S. Cl. .................................... 206/438
(58) Field of Classification Search ............... None
See application file for complete search history.

(56) References Cited

U.S. PATENT DOCUMENTS

| | | | |
|---|---|---|---|
| 4,321,781 A | 3/1982 | Hall | |
| 5,370,221 A | 12/1994 | Magnusson et al. | |
| 5,513,662 A * | 5/1996 | Morse et al. | 128/898 |
| 5,846,484 A * | 12/1998 | Scarborough et al. | 422/28 |
| 6,648,133 B1 * | 11/2003 | Blaschke et al. | 206/221 |

FOREIGN PATENT DOCUMENTS

| | | |
|---|---|---|
| DE | 297 05 993 U1 | 9/1998 |
| EP | 0 559 627 A2 | 9/1993 |
| EP | 0 928 612 A2 | 7/1999 |
| EP | 1 321 447 A1 | 6/2003 |
| EP | 1 325 713 A1 | 7/2003 |
| FR | 2 604 620 A1 | 4/1988 |
| FR | 2 702 661 A1 | 9/1994 |
| WO | WO 90/11066 A1 | 10/1990 |
| WO | WO 00/21489 A1 | 4/2000 |

(Continued)

OTHER PUBLICATIONS

Jianguo Li et al., High-strength aluminate cement produced by cold isostatic pressure, Journal of Materials Science, 2000, 5879-5883, v.35, Kluwer Academic Publishers.

*Primary Examiner*—Mary Lynn F Theisen
(74) *Attorney, Agent, or Firm*—Robert R. Deleault, Esq.; Mesmer & Deleault, PLLC

(57) ABSTRACT

A method and a device for moistening a porous medical material provide that the material is evacuated before it is moistened. The invention also covers a method of producing a porous medical material from bone particles that are compressed to a stable porous body. Said porous body is particularly suitable for being moistened in accordance with the method of the invention.

7 Claims, 3 Drawing Sheets

FOREIGN PATENT DOCUMENTS

| | | |
|---|---|---|
| WO | WO 00/50102 A1 | 8/2000 |
| WO | WO 01/76534 A1 | 10/2001 |
| WO | WO 01/76535 A1 | 10/2001 |
| WO | WO 02/05750 A2 | 1/2002 |
| WO | WO 02/16209 A1 | 2/2002 |
| WO | WO 03/008285 A1 | 1/2003 |

* cited by examiner

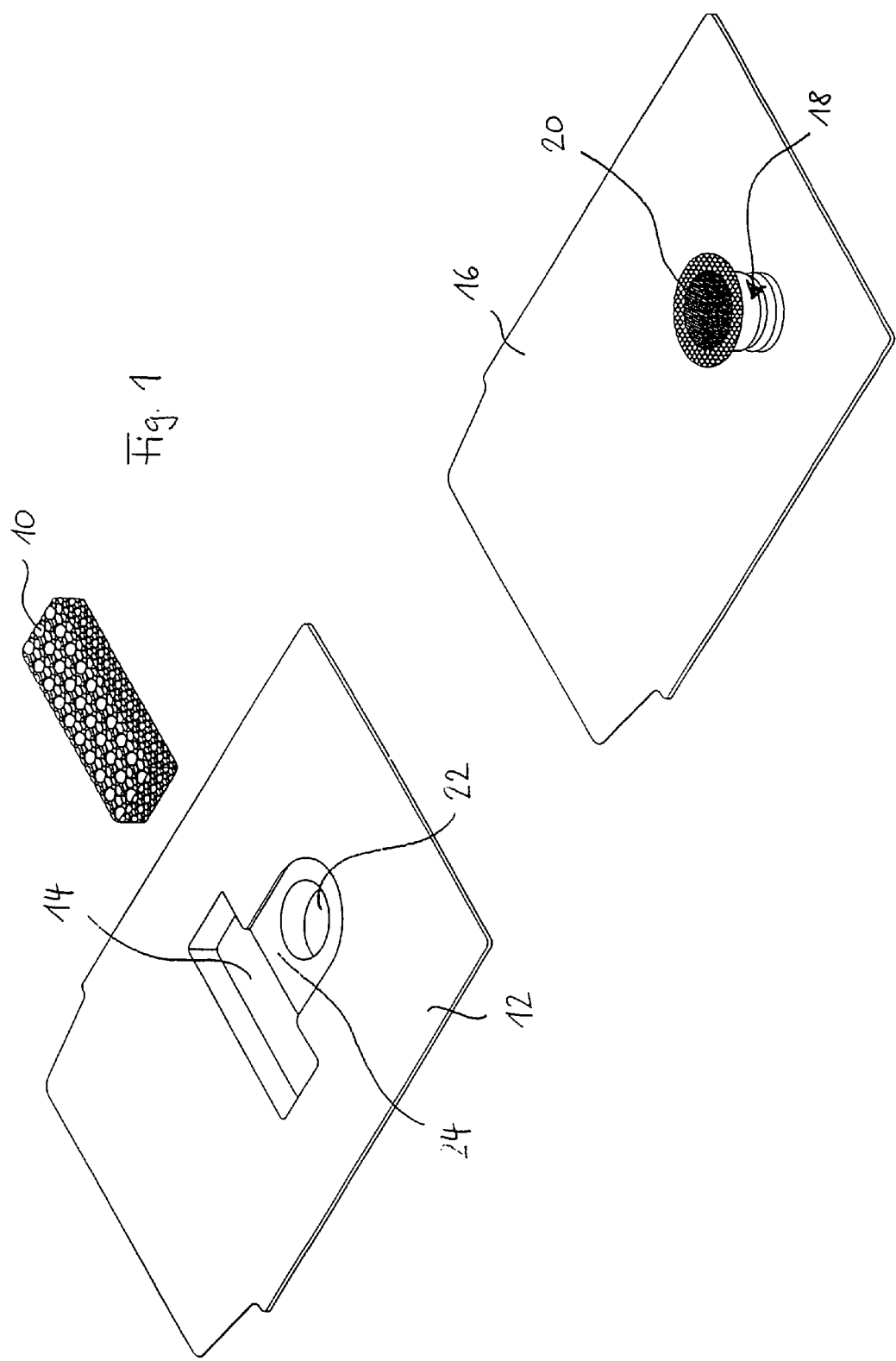

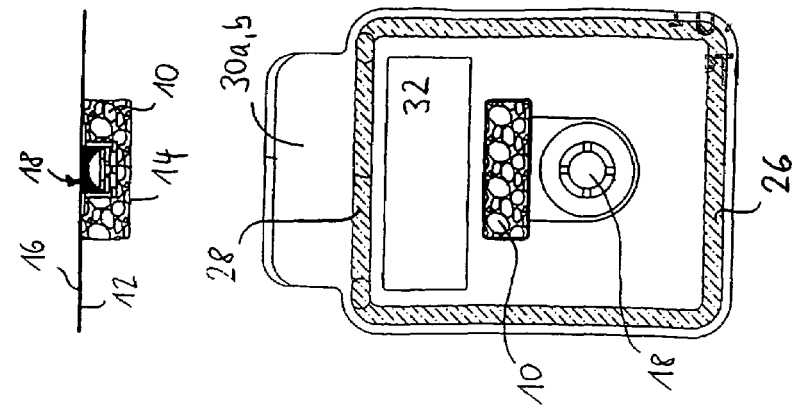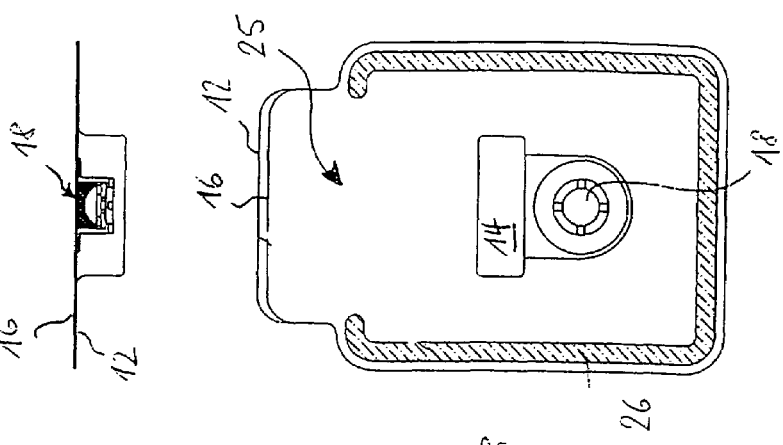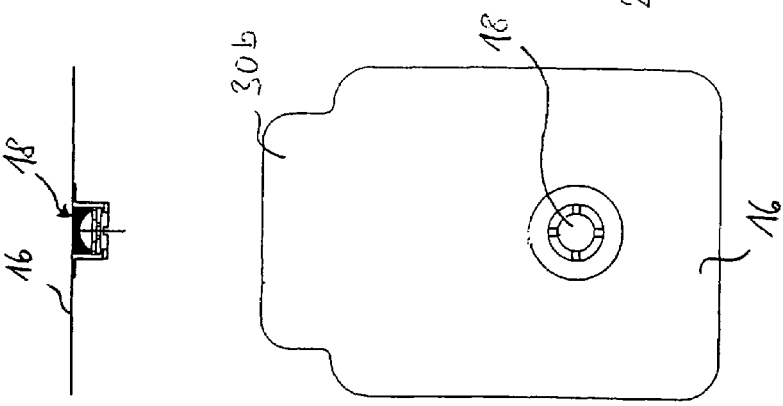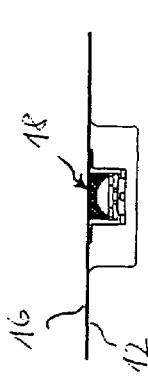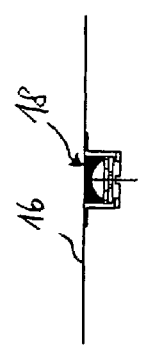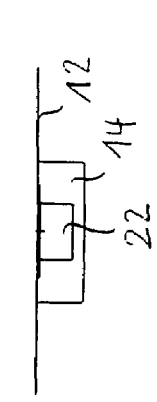

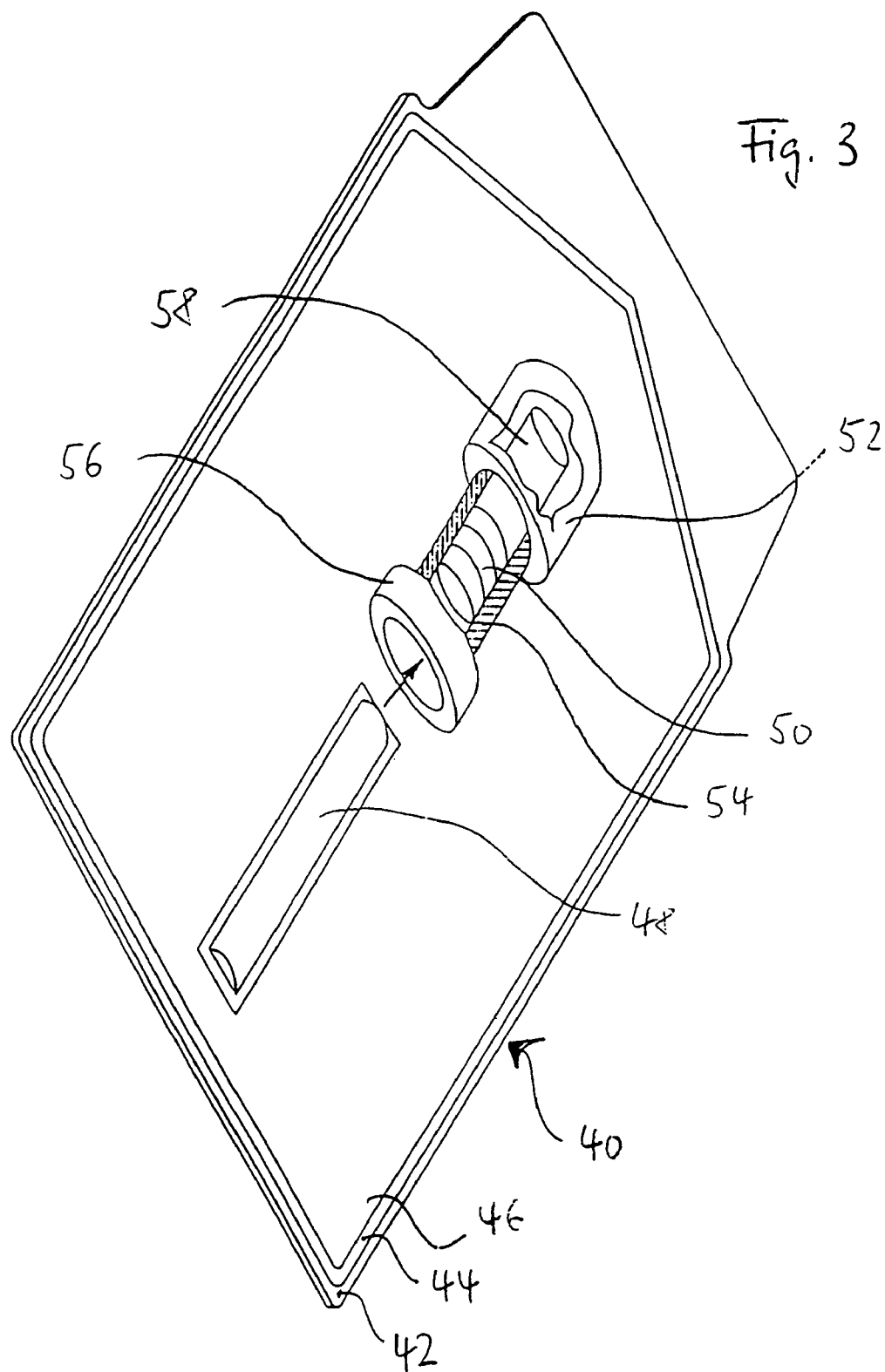

METHOD AND DEVICE FOR WETTING A MEDICAL IMPLANT OR TRANSPLANT

The invention relates to a method and a device for moistening a liquid-absorbing medical implant or transplant of substantially biological material.

An implant is a piece of tissue or other material inserted into a (human) body which remains in that body for at least some time.

Especially transplants, namely parts of a tissue or an organ, that are transplanted from another living being into a patient are a field of application of the present invention. Especially bone transplants are in consideration (human or bovine). It is also known in the state of the art to use particles of e.g. bone as medical filler material, for example in the dental field for filling extraction cavities. Such filling materials too are regularly rehydrated (i.e. moistened) before being used and the present invention is particularly suited for this purpose. Where it is stated in the present invention that the material is to be "essentially biological", this means that the material, at least for the greater part, was obtained from another living being or also from the patient himself. Nevertheless, the material may also contain a small amount of additives (up to a few percent, less than 10% as a rule) of non-biological material, i.e. material not obtained in the above-mentioned way.

In the following, the invention is explained in particular with a view to its use for moistening bone transplants. The application of the invention to other porous medical materials, such as biological and organic substances in general, results easily from this explanation.

In the prior art, the surgeon receives pieces of bone intended for transplantation in a sterile package. These pieces of bone are contacted with a moisturizer, e.g. a saline solution or plasma. The moisturizer may contain a medicament as additive, if required. This method of moistening implants or transplants is rather sophisticated and time-consuming. As a rule, it also requires too much moisturizer which means that there results an excess of moisturizer not made use of.

The invention is based on the object to provide a method and a device for moistening porous medical substances which enable a simple handling and an effective use of the moisturizer.

The method according to the invention and the device according to the invention provide that moistening of the porous medical substance is enhanced by a vacuum-induced suction effect.

The penetration of the moisturizer into the substance, namely the implant or transplant, is promoted according to the invention by a suction effect which produces a pressure drop that pushes the moisturizer into the implant or transplant. In addition to that suction effect, moistening of the implant or transplant can also be promoted by other effects, such as the capillary effect. This capillary effect is typically present anyway. However, the suction effect according to the present invention has a considerable advantage regarding the time needed for the moistening, and also the homogeneity of the moistening, i.e. the totally uniform penetration of the moisturizer into the material (of the implant or transplant). The invention also allows for an exact dosing of the amount of moisturizer such that excessive moisturizer (namely the amount of moisturizer not necessary for moistening the material) can be reduced substantially.

According to the preferred embodiment of the invention, it is provided that the implant or transplant is evacuated some time before it is moistened. In doing so, the suction effect is directly generated by the vacuum in the pores of the material.

In a modification of this embodiment, the suction effect can also be generated by evacuating a cavity which can be connected to the implant or transplant for gas communication. If that gas communication connection is generated shortly before or during the moistening operation and the moisturizer is supplied at another location to the implant or transplant (e.g. at the side opposite the gas communicating connection), the moisturizer, so to say, is drawn into and through the material of the implant or transplant by the suction effect and a homogeneous moistening inside the material is achieved. According to this embodiment, the material is evacuated immediately before it is moistened.

It is also possible to design the device in the manner of a container which can be evacuated and comprises walls that are essentially stable under vacuum. The porous medical material to be moistened can then be stored in that container, the material of the implant or transplant also being evacuated.

According to a particularly preferred embodiment, devices according to the invention are realized in the manner of a so-called elastic vacuum package.

According to another preferred embodiment of the device, there is provided a first chamber containing the implant or transplant and a second chamber containing a moisturizer, i.e. a liquid.

When these chambers can then optionally be connected with each other in liquid transferring manner, a vacuum in the first chamber effects, upon establishment of this connection for the purpose of moisturizing, that the moisturizer is sucked into the material of the implant or transplant.

Another preferred embodiment of the invention provides that the device comprises a septum for injecting a liquid for at least partially moistening the implant or transplant.

According to another preferred embodiment of the invention it is provided that the moisturizer contains a medicament.

It is also possible to combine the two afore-mentioned conceptions of "two-chamber system" and "septum" such that the device comprises a two-chamber system with a first chamber in which the evacuated porous material is contained, and a second chamber for the moisturizer. At an appropriate position, a septum may additionally be arranged through which, in addition to the moisturizer, a medicament can optionally be injected such that during moistening the medicament homogenously penetrates into the material together with the moisturizer. For example, the septum may be arranged such that the medicament can be injected into the moisturizer or into the moisturizer already flowing.

In the above described two-chamber system comprising a liquid-transferring connection therebetween it may be provided, for example, that first this liquid-transferring connection is interrupted and that this interruption, e.g. in the form of a membrane or the like, is adapted to be broken by the application of pressure from the outside. For example, if the device is realized as an elastic vacuum package, the user may, by applying pressure on the chamber in which the liquid is contained, cause the membrane to brake so that the moisturizer is sucked in the direction of the material to be moistened.

According to a further preferred embodiment which is particularly used in connection with a vacuum package, a cavity, e.g. in the form of a relatively stiff cartridge (as compared to the elasticity of the foil of the vacuum package), is provided downstream of the implant or transplant, such that excessive liquid remaining after the saturation of the porous material is sucked away from the porous material so that the amount of liquid actually delivered into the material is exactly the amount necessary and no liquid residues that might be troublesome remain on the material.

It is also possible to arrange the biological or organic material to be moistened in accordance with the present invention in an open hollow body, e.g. a cartridge. Such an arrangement in an open hollow body is, in particular, preferred when the material, even when evacuated under the effect of the outer air pressure (namely the atmospheric pressure), does not have sufficient dimensional stability. However, even material having dimensional stability with respect to the outer air pressure can advantageously be arranged in a hollow body. For example, such an arrangement allows for a supply of liquid into the material at an exactly defined position, and it can also guarantee that the moisturizer homogeneously penetrates through the biological or organic material to be moistened. Excessive moisturizer can also easily be removed by means of such a hollow body in a simple manner.

Moisturizers particularly taken into consideration are a saline solution or a plasma.

As medical porous material especially bones (spongiosa) or bone-like materials, e.g. materials made from bone, are taken into consideration. The transplants may be xenografts or allografts.

So-called spongiosa particles are known from the state of the art as far as they are used as so-called xenografts (Tutogen Medical GmbH, DE-91077 Neunkirchen am Brand, Germany). In this state of the art, the allografts and xenografts are offered to the physicist as particles having a specific size, in a conserved, radiation-sterilized form, normally as granulate.

Such a spongiosa granulate is used in a multitude of surgical fields of application, e.g. in orthopaedics, in neurosurgery, in the ENT field or also in dentistry. Dental fields of use comprise the augmentation of e.g. implants in extraction alveoles, the augmentation of fenestration defects, further the localized crest augmentation, in particular for the purpose of a later implantation, the crest reconstruction where prostheses are to be made, the reconstruction of defects, filling of extraction alveoles, filling of defects e.g. after a root apex resection, filling after a cystectomy or also filling after removal of impacted teeth, etc. Such granulates are also used after osteomy. Other fields of use are for example the filling of cranium defects or the application in the jaw region.

To this end, the surgeon has to moisten the granulates typically prepared and dehydrated previously. This "rehydration" is effected especially with physiological saline solution or thrombocyte-rich plasma to enhance the incorporation. When required, autogenic bone is mixed in.

The use of such prior art granulates does not only require that the surgeon has considerable experience and skill in rehydration, but also considerable skill in making implants in the above-mentioned fields of application. The demand that the surgeon has to have experience and skill implies on the other hand the danger of mistakes in the application.

Pressed tablets are further in consideration as porous bodies for the moistening of which the invention is also very well suited. Such tablets may for example be pressed from the above-described bone particles (so-called chips) in such a manner that the resulting tablet is porous. This method can generally be carried out with collagen-containing materials.

The invention relates also to a method of producing the above explained porous medical implants or transplants, in which bone material is comminuted to particles which are subsequently compacted to porous bodies. "Compacting" in this context means that the bone particles are compressed to such an extent that they make a dimensionally stable compound, which is porous throughout, without doing much damage to the microstructure of the bone.

The method of producing such compacted porous tablets from bone particles includes grinding the starting bone material, e.g. in a mortar, screening to obtain suitable particle sizes and subsequently compressing to a stable tablet. It showed (surprisingly) that a relatively dimensionally stable porous tablet can be obtained merely by compression. If this tablet is subsequently rehydrated, preferably by way of the above-described vacuum-suction effect, for example, it swells somewhat and thus can easily be molded so that the surgeon can fit in and mould the tablet or parts thereof (it is also possible to provide tablets of different sizes) directly at the site of application when necessary.

The invention provides for a remedy in two aspects. On the one hand, the porous body of spongiosa particles compacted according to the invention does as such already simplify the application in a multitude of fields of application, e.g. those mentioned above. On the other hand, the porous body formed in this manner can be rehydrated much easier and better than the granulate, a rehydration according to the evacuation technique described above being particularly preferred. In this context, the term "rehydrating" has to be understood—in line with the general medical usage—in a broader sense and comprises moistening with a suitable liquid, not only with water or a salt solution, in general. "Rehydrating" in this context means in particular also "moistening with (blood) plasma".

In the following, embodiments of the invention are explained in more detail with reference to the drawings. In the drawings FIG. 1 shows a device for moistening a porous medical material, the device being disassembled;

FIGS. 2A, 2B, 2C and 2D show a device according to FIG. 1 in different stages of assembly, and FIG. 3 shows a further embodiment of a device for moistening an absorbent medical material, said device comprising a vacuum package.

The device shown in the figures is, in particular, suitable for moistening a porous bone transplant 10 that was produced previously in a known manner and rehydrated. Such a transplant may e.g. have dimensions of typically some centimeters. The porous bone transplant 10 may be obtained e.g. without comminution (generation of chips) merely by sawing bones or also in accordance with the above explained compacting of particles or chips. To say it generally, the bone transplant 10 used in this embodiment represents a porous medical body of biological origin.

The device comprises a base 12 made e.g. from transparent plastic material. In the embodiments shown, the base 12 is made from a so-called blister material, which has some elasticity and nevertheless has sufficient stiffness in order to remain dimensionally stable, depending on the size of the transplant 10, upon the application of a vacuum in the inside upon an area of some square centimeters with respect to atmospheric pressure.

The base 12 comprises a trough 14 into which the transplant 10 fits exactly. An upper member 16 closes the trough 14 in air-tight manner against the outer atmosphere in the manner of a cover. A septum 18, known as such, (see also FIG. 28) is also fastened to the upper member 16 in air-tight manner and protrudes in FIG. 1 downwards into a second trough 22 formed in the base 12. The septum 18 can be of known type and comprises at the top a membrane 20 through which an injection needle (not shown) can be inserted. The terms "above" and "below" are here understood in the sense of the usual position of the device when in use.

The said troughs 14 and 22 form, when the upper member 16 is placed on the base 12 in air-tight manner (see further below), a system of two chambers connected with each other by a channel 24. In the embodiment shown, the channel 24 has the shape of a relatively flat and wide depression in the base 12.

FIGS. 2A to 2D show individual stages of assembly of a device according to FIG. 1. FIGS. 2A to 2D show, below, a top view upon the base and the upper member, respectively, and above a cross section perpendicular to the main plane of the base at the level of the trough 22; the trough 14 (which would actually not be included in the cross section) being shown additionally.

FIG. 2A shows the base 12 (blister) made from a transparent foil having a thickness of 0.2 to 0.4 mm. The dimensions of the troughs 14, 22 are adapted to the needs, i.e. the dimensions of the transplant 10 and the septum 18 to be provided, respectively.

FIG. 2B shows the upper member 16 including the air-tight, attached septum 18. The upper member 16 may, e.g., be manufactured from a cover foil somewhat more elastic as compared to the base 12, the foil having a thickness in the range of 0.1 to 0.2 mm.

FIG. 2C shows the base 12 and the upper member 16 in a partly assembled state. A welding stripe 26 connects the base and the cover partly wherein a certain area 25 is, at this stage, non-welded such that a vacuum pump (not shown) can suck air from the troughs 14, 22 through the open area 25. This way, the base and the upper member are connected in surface contact and a transplant 10 positioned in the trough 14 is also evacuated. Furthermore, the trough 22, assigned to the septum 18, is also evacuated, together with the septum, through channel 24 between troughs 14 and 22.

The base 12 and the upper member 16 are sufficiently stable to allow the evacuation (a modified embodiment comprising a somewhat more elastic material in the manner of a vacuum package is described further below).

After evacuation, in the state according to FIG. 2C, another welding stripe 28 is e.g. thermally activated or applied. It seals the entire space between the base 12 and the upper member 16, except for two pull-off edges 30a, 30b, in an air-tight manner, together with the above-mentioned welding stripe 26.

A label 32 is applied to the upper member 16 in order to give the user the necessary information about the transplant 10. For moistening the transplant 10, the user injects through the membrane 20 of the septum 18 a suitable liquid, e.g. a saline solution or a plasma, if required with added medicaments. The size of the trough 22 is adapted to the size of the septum such that the liquid is directly transferred through the channel 24 into the trough 14 and, therefore, into the transplant 10.

Since the size of the trough 22 is adapted to the outer dimensions of the septum and, furthermore, the size of the trough 14 is adapted to the size of the transplant 10, the user can adapt the supply of liquid exactly to actual requirements, namely supply only so much liquid as is necessary for moistening the transplant 10. For example, the amount of liquid to be supplied can be indicated to the user on the label 32.

The embodiment illustrated by FIGS. 1 and 2 can e.g. be modified such that the material used to cover the said parts is a vacuum package having full elasticity. Such an embodiment comprising a vacuum package is shown in FIG. 3 schematically. The vacuum package 40 comprises a flat carrier 42 upon which two foils 44, 46 are laminated, one on top of the other. Between the foils 44, 46 a liquid reservoir 48 is formed like a cushion tightly filled with a liquid by which a medical, fluid-absorbent material 50 is to be moistened. The material 50 is located in a cartridge 54 that is sufficiently stiff in order to protect the material 50 extensively against forces from the outside such as extreme pressure or the like. Preferably, the material of the cartridge 54, though it has sufficient dimensional stability, also has some elasticity. A ring 56 at the opening of the cartridge 54 protects the cartridge against squeezing and at the other end of the cartridge 54 an also relatively stiff container 52 for excessive liquid is provided into which a pipe 58 protrudes through which the excessive liquid enters the container 52. The inside between foils 44, 46, including the cartridge 45 and the container 52, is evacuated.

For moistening the liquid-absorbing material 50, namely e.g. a porous body of the above type, the user presses the liquid container 48 (e.g. with the fingers) such that a predetermined breaking point to the cartridge 54 breaks. Said breaking point is positioned approximately at the location of the arrow shown in FIG. 3 between the foils 44 and 46 so that liquid from the container 48 passes through the ring 56 into the inside of the cartridge 54 and the rehydration in the sense as explained above is performed there. If the interior of the container 52 is evacuated as well, the pipe 58 causes also a certain suction effect into the interior of the cartridge, and excessive liquid is removed from the material to be moistened. An exact control of the moistening operation is possible in this way if the volume of the container 52 and therefore, i.a. also the said suction effect, is adapted to the material 50 to be moistened.

The embodiment of FIG. 3 as well can be modified to the effect that a septum for injecting the liquid is arranged between the elastic foils 44, 46 of the vacuum package 40, in this respect similar to the embodiment of FIGS. 1 and 2.

As mentioned in the beginning, the invention can also be realized with a relatively stiff container in which the porous implant or transplant is arranged in an evacuated manner.

The devices and methods described above can be modified as follows:

Above, it was assumed that the gas evacuated from the porous material is air. According to a modified embodiment of the invention, a protective gas is used to fill temporarily the porous material. For example, an inert gas may be used, preferably however, a gas which can be dissolved in the liquid used to moisten the material. For example, $CO_2$ is a preferred gas used to fill more or less the cavities in the porous material. $CO_2$ is very well soluble in a multitude of liquids used in medical applications, water in particular. The use of a protective gas to fill the porous material has the advantage that during storage of the material prepared in this manner the protection is more effective. During storage, the protective gas is held in the chamber which also contains the porous material, at a pressure that can be selected as follows:

If the pressure of the protective gas is smaller than the atmospheric pressure, there will be a suction effect regarding the liquid, when the material is moistened. If the pressure of the protective gas is selected larger than atmospheric pressure, the protective effect is enhanced.

If the pressure of the protective gas corresponds to atmospheric pressure, the filling of the gas into the porous material is eased.

The actual selection of the pressure will be made depending on the circumstances and the desired effect.

The afore-mentioned variants of the invention using a protective gas can be combined with the above-described embodiments of the present invention illustrated in FIGS. 1 to 3. For example, the protective gas may be filled into the porous material in the factory manufacturing the device containing the material; in that case the material has to be moistened later in a hospital or the like.

Also, the use of a protective gas can be combined with the above-described system in which a cavity is provided downstream of the material such that a vacuum can be applied to said cavity which is in fluid connection, at least temporarily, with the chamber containing the porous material, so that excessive liquid and, at least partly, the protective gas are sucked away from the material such that both the excessive liquid and at least some protective gas are transferred away from the porous material into said cavity, so that the porous material is perfectly homogeneously moistened without any excessive liquid which may be troublesome during the medical use of the material.

The invention claimed is:

1. A device for moistening an essentially biological medical implant material (10) the device comprising a casing (12, 16), a first evacuated chamber (14, 54) in the casing, means (18, 20) to inject a liquid into the casing wherein the material is inserted into the first chamber (14), a second chamber (22, 52) in the casing, means to evacuate the first and second chambers, and channel fluidly connecting the first chamber to the second chamber.

2. A device according to claim 1, wherein the second chamber (22) is provided with a membrane (20) for insertion of an injection needle.

3. A device according to claim 1 wherein the casing is composed of a sheet-formed base (12) and a sheet-formed cover (16)attached to each other.

4. A device according to claim 1, wherein means (25) are provided to evacuate the first chamber and the second chamber simultaneously with the material (10) being inserted in the first chamber (14).

5. A device according to claim 1, wherein the second chamber is located at a side of the material which is opposed to a side of the material being inserted in the first chamber.

6. A device according to claim 1, wherein the casing comprises a container for the liquid.

7. A device according to claim 6, wherein the container is connectable to the first chamber by breaking a point of fracture.

* * * * *